United States Patent [19]

Buckner

[11] Patent Number: 4,735,754

[45] Date of Patent: Apr. 5, 1988

[54] METHOD FOR FABRICATING ARTIFICIAL BODY PARTS

[76] Inventor: Horst Buckner, 2829 W. Northwest Hwy., Westminster Bldg., Ste. 7001, Dallas, Tex. 75220

[21] Appl. No.: 897,335

[22] Filed: Aug. 18, 1986

[51] Int. Cl.⁴ .................. B29C 33/40; B29C 39/44
[52] U.S. Cl. ................................. 264/40.1; 156/62; 264/135; 264/154; 264/156; 264/221; 264/222; 264/223; 264/227; 264/317; 264/338; 623/27; 623/28; 623/31; 623/32; 623/55; 623/DIG. 1
[58] Field of Search ............... 264/40.1, 69, 71, 135, 264/156, 221, 222, 223, 225, 226, 227, 317, 338, 154, DIG. 30, DIG. 44; 156/57, 61, 62; 623/27, 28, 31, 32, 53, 55, 57, DIG. 1

[56] References Cited

U.S. PATENT DOCUMENTS

| | | | |
|---|---|---|---|
| 3,520,002 | 7/1970 | Wellington | 264/222 X |
| 3,909,855 | 10/1975 | Barredo | 623/32 |
| 3,953,900 | 5/1976 | Thompson | 623/27 X |
| 4,619,661 | 10/1986 | Axelsson | 623/55 |

Primary Examiner—Jeffery Thurlow
Assistant Examiner—Leo B. Tentoni

Attorney, Agent, or Firm—Jerry W. Mills; Roger N. Chauza

[57] ABSTRACT

Disclosed is a method of fabricating a prosthetic member (112) having personalized features of the patient, and being formed to provide an individualized fit to the patient's extremity (18). A rigid jacket (30, 32) is first formed around the uninsured foot (10) and the amputated extremity (18). The limb characteristics are impressed into an alginate (44) lining within the jackets (30, 32). A stone material poured into the alginate lining (44) forms stone models (48, 50) of the patient's limbs. A wax preliminary model (64) is sculpted in the likeness of the stone foot model (48) and used to form final stone mold halves (100, 102). The contour of the stone extremity model (50) is adjusted according to the tissue texture of the patient to provide an individualized fit. A gelatinous silicone is injected inside the final mold (100, 102) and allowed to form around the extremity model (50) to thereby provide the body of the prosthetic member (112) and the conformal sleeve (132). During the silicone curing process, silicon material is selectively removed from the member (112) to provide the desired flexibility.

36 Claims, 3 Drawing Sheets

METHOD FOR FABRICATING ARTIFICIAL BODY PARTS

TECHNICAL FIELD OF THE INVENTION

The present invention relates in general to methods and apparatus for fabricating artificial body parts, and more particularly relates to the fabrication and fitting of prosthetic members to body extremities.

BACKGROUND OF THE INVENTION

The primary concerns of a person or amputee having the need for a prosthetic body part are twofold. First, it is highly important to the amputee that the prosthetic member appears as natural as the missing body part. Where the missing body part is a hand or a foot, it is desirable for pusposes of symmetry that the prosthetic replacement appears essentially as the mirror image of the other corresponding body part. Secondly, for purposes of comfort, fit and reliability and function, it is highly important that the prosthetic member conforms with the contour of the amputated limb or extremity. With a proper fit, the correct attachment of the prosthetic member to the extremity is assured, and thus the constraints on the activity of the person are minimized.

The fabrication of an artificial body part to reproduce the natural skin tones, shapes, sizes and idiosyncrasies of the missing body part are dependent, in part, upon the skill of the craftsman. The process for forming a foot or hand, for example, depends on the craftman's ability to make a series of molds to form a plastic or rubber prosthetic member. Single molds heretofore fabricated were made from a metal material for producing numerous prostheses for different patients. The molds were, however, not individually stylized for each patient and thus would not uniquely match the other corresponding uninjured body part.

The prior techniques employed in attaching a prosthetic member to an extremity required a relatively large surface area of the limb to produce a frictional engagement, thereby providing a reliable attachment of the member to the extremity. By the use of the techniques heretofore known for attaching a prosthetic member to a limb, it was also advantageous to use the irregular contours of the limb for additional frictional engagement. For severe toe or forefoot injuries, disease or deformities, surgeons still amputate the complete foot above the ankle to provide a stump considered ideal for acceptance of a prosthesis, made by conventional techniques. In this manner, it was thought that the prosthetic member could be conformed around the irregular part above the ankle to thereby provide an improved attachment of the member to the stump. A need therefore exists for a method and technique which eliminates the unnecessary and excessive amputation which removes a part of the uninjured foot and part of the ankle.

Because of the significance placed on a person's appearance, it is of paramount importance that prosthetic members attain a lifelike appearance, that they be easily reconstructed for replacement, and that an improved attachment to the extremity be provided. It may be seen from the foregoing, that a need has arisen for such an improved technique for constructing prosthetic members which avoid or substantially reduce the shortcomings of the techniques and apparatus heretofore known.

SUMMARY OF THE INVENTION

In accordance with the principles and concepts of the present invention, there is provided an improved method of forming individualized fitting artifical or prosthetic members. The method of preparing a prosthetic member according to the invention, for example a foot, includes first, forming a plaster bandage jacket around both the uninjured foot and the corresponding injured extremity. The plaster bandages are spaced away from the surface of the uninjured foot, ankle and lower leg, and injured extremity a predetermined distance. A conformal mixture of material, such as dental alginate, is forced into this space. The alginate material provides the first or preliminary molds with a negative impression of the exact likeness of the uninjured foot and the injured extremity.

The patient's foot and injured extremity are then removed from the respective first molds, and the cavities are filled with a slurry of plaster of paris or other similar stone material or plastics. When the plaster of paris hardens, the outer surface thereof provides a model of the uninjured foot and the injured extremity. A stone model of the extremity and the uninjured foot provide the craftsman with models necessary to continue the fabrication of the prosthetic member.

A large amount of softened wax is attached to the stone model of the extremity and is sculpted according to the features of the stone model of the uninjured foot. Of course, the sculpting is accomplished to provide a mirror image foot, rather than an exact duplicate cf the uninjured foot. The wax model provides an exact likeness from which the prosthetic foot will be formed. The wax foot model and attached stone extremity are then set into a flask, with the sole of the foot being orthogonal to the bottom of the flask. The flask is partially filled with a slurry of plaster of paris to cover the left halves of the wax foot and attached stone extremity. The other half of the mold is formed in a similar manner to provide two mold halves. The mold halves are boiled in water to remove the wax material.

The stone halves of the mold are used for forming the prosthetic member by mating together the mold halves and packing uncured silicone within the resulting mold cavity. The stone extremity remains positioned in the mold halves, as was when attached to the wax model. The silicone conforms with the mold cavity and takes on the exact likeness of the previous sculpted wax foot. Also, a sleeve forms around the stone extremity model and conforms to the exact shape of the stone extremity model. The mold and silicone are boiled for a period of time sufficient to cure an outside layer of the silicone, leaving the interior part thereof yet uncured.

The mold halves are removed, together with the stone extremity model, and slits are cut into the silicone foot member at preselected locations. A certain amount of uncured silicone is extracted therefrom. This prevents a stiff rubbery foot member and allows the foot to function and appear natural. The mold halves and the stone extremity model can be reused as desired.

The visible and aesthetic characteristics of the foot, such as blood vessels, hair, toenails, etc., are then painted on the surface of the silicone prosthetic foot, including the proper color of the flesh. A layer of clear silicone is painted thereover to preserve these features of the foot.

In accordance with another technique for fabricating prosthetic members, a member is formed having an individualized fitting element attached to a universal prosthetic foot or hand member.

BRIEF DESCRIPTION OF THE DRAWINGS

Further features and advantages of the present invention will become apparent from the description of an illustrative technique thereof, taken in conjunction with the accompaying drawings, in which.

DETAILED DESCRIPTION OF THE INVENTION

Referring to the drawings, there are shown the steps in preparing a prosthetic member according to the invention. For purposes of example only, the method will be described in connection with the formation of a prosthetic left foot. FIGS. 1-6 illustrate the advance in the art and science of prosthetics wherein a permanent stone model is fabricated including all the features and characteristics of both the injured extremity and the uninjured member.

Figure 1:
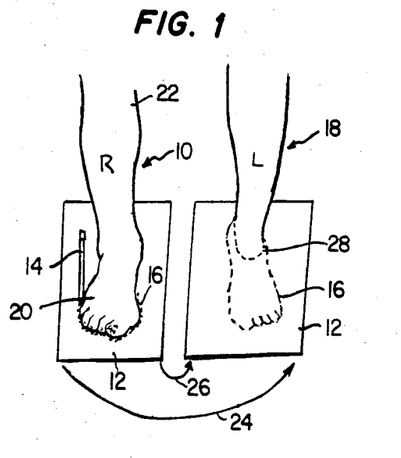
FIG. 1 is illustrative of the technique for assuring the proper orientation of the proposed prosthetic member to the amputated limb or extremity.

With reference first to FIG. 1, the peripheral shape of the uninjured right foot 10 is outlined on a translucent paper 12 by a pencil 14. The outline or podograph 16 forms a record for aligning the prosthetic member in the same angular position with respect to the amputated limb extremity 18, as the uninjured foot 20 is aligned with the calf 22. In this regard, it is important that the paper 12 be aligned orthogonal to the trunk of the patient's body so that any toe-in or toe-out of the right uninjured foot 20 can be reproduced by aligning the prosthetic member in a similar manner with respect to the amputated limb extremity 18. Other foot disorders or deformities can be similarly reproduced, if desired, to provide a symmetry between the right and left limbs.

After the podograph 16 has been recorded on the paper 12, the paper 12 is rotated 180° as shown by arrows 24 and 26, and superimposed under the amputated limb extremity 18. The podograph outline 16 is clearly visible through the paper 12. A second outline 28 is made with a color pencil around the extremity 18 at the desired location within the podograph 16. It can be seen that if the uninjured foot 20 has a toe-in or toe-out, such a characteristic will be transformed to the other limb, due to the 180 degree rotation of the paper 12.

Figure 2:
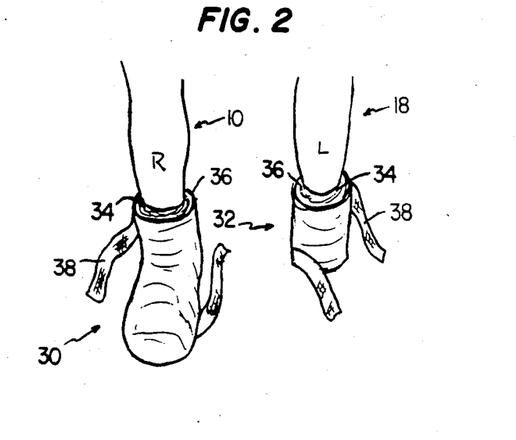
FIG. 2 illustrates the next step in the process in which plaster bandages are wrapped around a stuffing material to form a rigid jacket spaced from the extremity and the uninjured foot.

FIG. 2 illustrates the initial steps in preparing a pair of molding jackets 30 and 32 around the respective uninjured member 10 and the amputated limb extremity 18. The molding jackets 30 and 32 are formed somewhat oversized from the members which are encompassed. In order to accomplish this, a uniform layer of material about three-eights inch thick is first wrapped around the uninjured member 10 and around the amputated limb extremity 18. In practice, it has been found that three pairs of woolen socks provide the desired thickness. Lastly, and on top of the woolen socks 34, a nylon or other smooth material is wrapped. A relatively nonporous or smooth material is preferred so as to provide a nonadhering surface for plaster bandages 38 to be subsequently wrapped around the nylon material 36. A thin coating of Vaseline, or other oily substance, facilitates the nonadherence of the nylons 36 to the plaster bandages 38.

Lengths of conventionally obtainable plaster bandages 38 are wetted to dissolve the plaster material within the gauze bandage, and then wrapped several layers thick around the nylon-clad socks. The uninjured member 10, as well as the amputated limb extremity 18 undergo both of these steps to form the respective molding jackets 30 and 32. The plaster bandages 38 are wrapped around the uninjured member 10 and the amputated limb extremity 18, including the underside thereof, to a distance of about ten centimeters above the ankles. The plaster bandages 38 remain wrapped around the patient's limbs until the bandages 38 become dry and rigid. The rigid molding jackets 30 and 32 are then cut vertical on the backside, in the same locations as shown by dashed lines 40 and 42 in FIG. 4.

The patient's uninjured member 10 and amputated limb extremity 18 are then carefully removed from the molding jackets 30 and 32. The socks 34 and nylons 36 are discarded. The molding jackets 30 and 32 thus form a rigid shell which is oversized compared to the diametric dimensions of the uninjured member 10 and the amputated limb extremity 18.

Figure 3:
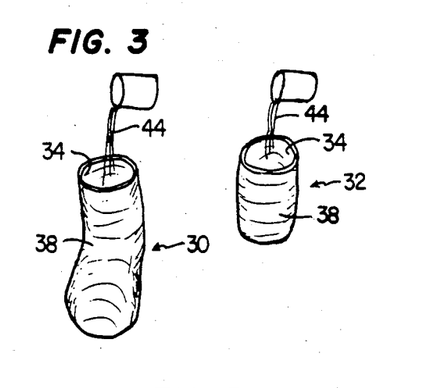
FIG. 3 shows the filling of the plaster bandage jackets with a contour-conforming material.
Figure 4:
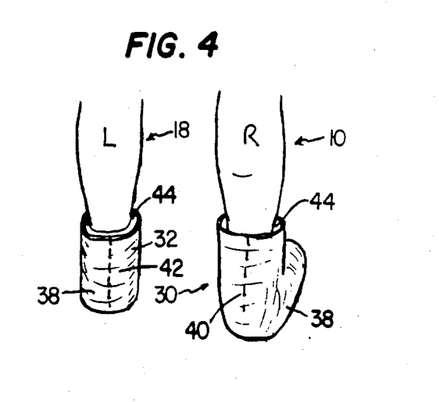
FIG. 4 shows the step of forming negative impression molds of both the extremity and the uninjured foot within the contour-conforming material.

In accordance with the invention, and as shown in FIG. 3, each molding jacket 30 and 32 is substantially filled with a contour-conforming substance 44, such as gelatinous colloid or a dental alginate. Alginate is a substance which provides an excellent impression of the surface against which it is pressed. The patient's uninjured member 10 and amputated limb extremity 18 are then inserted within the respective molding jackets 30 and 32. This is not overly difficult as the molding jackets 30 and 32 are somewhat oversized, and split so that the limbs can be inserted before the contour-conforming substance 44 becomes congealed. The molding jackets 30 and 32 may be agitated slightly with respect to the uninjured member 10 and the amputated limb extremity 18 so as to allow the contour-conforming substance 44 to work itself into contact with all surfaces of the covered limbs. The contour-conforming substance 44 is allowed to congeal, whereupon a highly accurate negative impression is formed on the inside surface thereof. The wall thickness of the contour-conforming substance 44 is uniform, thus assuring a uniform shrinkage and an accurate representation of contours of the extremity and the uninjured foot. This is highly essential to the proper fit of a prosthetic member to the amputed limb or extremity. The foregoing contrasts with prior methods used by prosthetists, wherein a contour-conforming substance of nonuniform wall thickness was used, or a plaster of paris material was directly utilized as the mold impression material.

Figure 5:
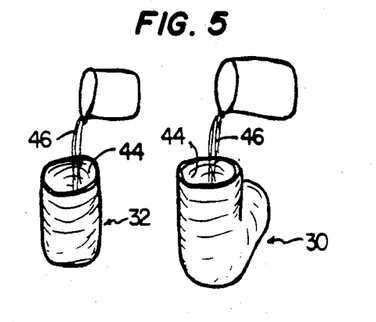
FIG. 5 illustrates the formation of stone models of the extremity and the uninjured foot by filling the negative impression molds with a hardening material.

Proceeding with the techniques of the present invention, and as noted in FIG. 5, the cuts 40 and 42 are closed, and liquified plaster of paris 46 is poured into the cavity formed by the contour-conforming substance 44. Casting materials other than plaster of paris may be used, such as a dental stone. The molding jackets 30 and 32 may again be agitated to assure that the plaster of paris 46 provides a full contact interface to the contoured surfaces of the negative impression comprising the contour-conforming substance 44. The plaster of paris or other stone material is allowed to completely harden.

It can be appreciated that the hardened plaster of paris 46 formed in accordance with the foregoing technique forms respective stone models 48 and 50 of the uninjured member 10 and the amputated limb extremity 18. Moreover, because the uniform shrinkage of the contour-conforming substance 44, the stone models 48 and 50 are exact replicas as to size, shape and texture of the uninjured member 10 and the amputated limb extremity 18. All further major steps in accordance with the method of the invention are conducted using the stone models 48 and 50, rather than the patient.

Figure 6:
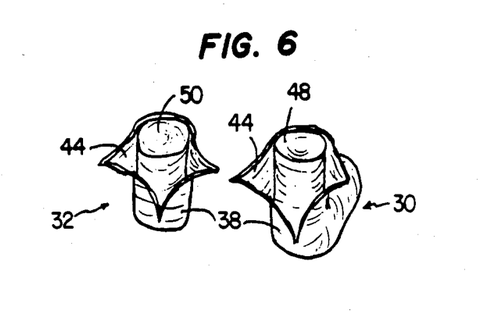
FIG. 6 illustrates the removal of the plaster bandage jacket and the contour-conforming material from both the stone models of the extremity and the uninjured foot.

As shown in FIG. 6, the molding jackets 30 and 32 as well as the interior lining comprising the contour-conforming substance 44 are discarded. In order to remove the molding jacket 30 from the uninjured member 10, the jacket 30 may be damaged to such an extent that it can no longer be used. However, from the foregoing it can be seen that with the intermediate step of forming a negative mold with the contour-conforming substance 44, a stone model is provided which is much improved over the molds heretofore formed.

When the techniques of the present invention are utilized in connection with prosthetic foot members, it is customary to use a sandal strap or shoe to cover the circumferential edge where the prosthetic member interfaces with the patient's limb. Accordingly, to illustrate the principles of the invention, the stone extremity model 50 is positioned within a pair of sandals, and preferably the type of sandals having a front strap. The foregoing is illustrated as a prosthetic member made in accordance with the invention described herein includes all the attributes of the uninjured member, and thus cannot be detected as an artificial member, even when covered only by sandals.

Figure 7:
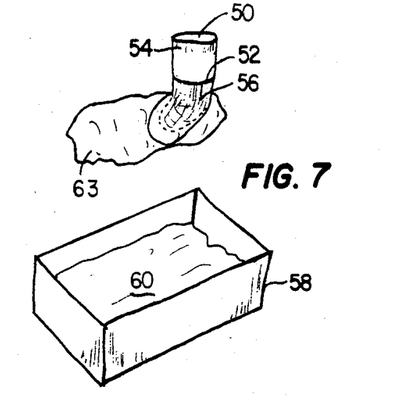
FIG. 7 depicts the formation of a preliminary artificial member by the building of wax on the stone extremity model.
Figure 8:
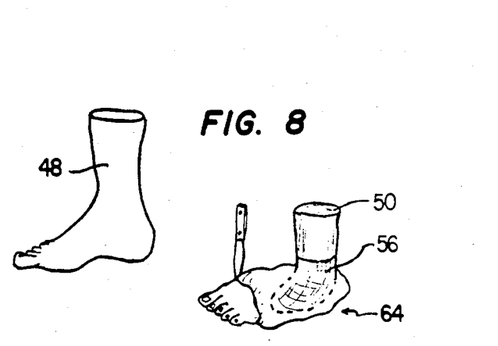
FIG. 8 illustrates the sculpting of the wax to form the preliminary artificial member in accordance with the features of the stone model of the uninjured foot.

When the stone extremity model 50 is positioned in a sandal (not shown), an outline 52 is made on the top of the sandal strap (or shoe) for providing an upper marginal edge of the finished prosthetic member. In this manner, the upper marginal edge of the prosthetic member can be substantially hidden under the sandal strap or the shoe material. The margin outline is shown in FIG. 7 as reference character 52. The technique for forming a preliminary artificial member is illustrated in FIGS. 7 and 8.

The stone extremity model 50 is treated with a separator material, such as oil or Vaseline, and then covered with a reinforcing material 56. A stocking mesh reinforcing material, such as perlon tricot, is suitable for use as the reinforcing material 56. The reinforcing material 56 is wrapped around the stone extremity model 50 so as to completely cover it, including the bottom thereof. A container 58 of molten wax 60 is prepared, and the stone extremity model 50, covered with the reinforcing material 56, is initially brushed with the molten wax. The thinly covered wax model 50 is then repeatedly dipped into the molten wax 60 to form a plurality of wax layers covering the reinforcing material 56. The layers are formed thicker toward the sole, thinner toward the ankle. The wax 60 becomes embedded within the reinforcing material 56 and saturates the material.

The unit is then placed on the paper 12 within the colored outline 28 drawn previously around the amputated limb extremity 18. Corrections around the horizontal axis of the extremity, according to previous evaluations, are performed with wax build-ups at desired locations. Various corrections may include, for example, an additional build-up of wax under the heel to provide a lift to the patient's hip bone. This procedure forces a desired elevation in the patient's hip bone which offsets a tendency in leg amputees of the hip bone to sag because of the missing extremity. Lower back pain and spinal distortion are thereby alleviated.

When the wax globule 63 and the stone model 50 are correctly oriented with respect to the paper record 12 (rotated 180°), wax forefoot and toes are manually added to the globule 63 with additional softened wax. This is accomplished by using the outline 16 previously drawn on the paper 12. To provide a mirror image, the position of the toes of the left foot are sculpted in a reverse fashion with respect to the toes on the right foot. The other contour surfaces on the left wax foot are also reversed with respect to those on the right uninjured foot. The wax model is then allowed to cool and harden on the paper according to the normal consistency of wax material.

Next, the wax model is sculpted as shown in FIG. 8, according to the stone model 48 of uninjured member 10. The personal characteristics of the uninjured member 10, including the toe shape, toenails, veins, etc., are sculpted by the craftsman out of the wax globule 63.

When the wax model 64 is completed to the satisfaction of the craftsman, a cut is made through both the wax model 64 and reinforcement material 56. The cut is made from the top of the wax model heel to the front of the sole. The severed parts of the wax model 64 and reinforcement 56 are separated sufficiently to remove the stone extremity model 50. It can be appreciated that the reinforcement 56 allows a certain degree of flexing of the wax without cracking or breaking. The preliminary artificial wax model 64 may then be fitted on the patient's amputated limb extremity 18. The cut in the wax is held closed with tape. A sandal, or shoe, may be tried on the wax model 64 to check whether the sandal strap coincides with the previously marked top margin 52. Also, the hip bone elevations of the patient can be checked while the patient stands. At this stage, changes can be made to the preliminary wax model 64 to correct for the general shape, size or to add particular cosmetic characteristics. When the external features of the wax model 64 are satisfactory to the craftsman and patient, the temporary wax model 64 is removed from the patient. Any sensitive areas which the patient indicates exists on the amputated limb extremity 18 are marked on the stone extremity model 50. Such areas are noted both on the side and underside surfaces of the stone extremity model 50.

In accordance with an important feature of the invention, areas which are indicated as sensitive to the patient are enlarged outwardly by a small amount of plaster of paris. However, in order to bond unset plaster or paris to the hardened stone extremity model 50, a number of holes are first drilled in the areas of sensitivity. The application of new plaster of paris to the drilled areas fills in the holes and allows the new plaster of paris to firmly adhere to the stone extremity model 50. It will be understood from the description which follows that the build-up areas on the stone extremity model 50 are transformed in the final prosthetic member into corresponding concave areas. A slight additional amount of room is thereby provided in the final prosthetic member to accommodate the sensitive areas of the patient's amputated limb extremity 18.

Figure 9:
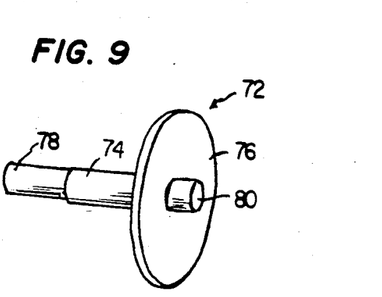
FIG. 9 illustrates a tool for gauging the softness of the patient's extremity tissue.

In accordance with another feature of the invention, the consistency of the tissue on the patient's amputated limb extremity 18 is ascertained for appropriately contouring the inner surface of a sleeve section of the prosthetic member. This is important with regard to comfort and fit, as the sleeve of the prosthetic member fits over and engages with the amputated limb extremity 18 of the patient. A gauge 72 suitable for use in determining tissue consistency is shown in FIG. 9. The gauge 72 includes a tubular section 74 integral with a flanged base plate 76. Slidable within the tubular section 74 is a graduated slide gauge 78. The slide gauge 78 has a blunt end 80 which is pressed against the tissue of the extremity 18.

In operation, the slide gauge 78 is withdrawn (to the left in the figure) so that it does not protrude beyond the base plate 76. The base plate 76 is then held flush against one spot of the tissue of the patient, and the blunt end 80 of the slide gauge 78 is pushed toward the patient. The base plate 76 is then released or eased until it lifts off the tissue. A number of such measurements are taken at about 5 mm spacings over the entire surface of the amputated limb extremity 18 which is to be covered by the sleeve of the prosthetic member. At corresponding locations on the stone model 50, holes are drilled to the exact depth as measured by the gauge 72. The lower portion of the stone extremity mold 50 should thus have a gridwork of holes spaced about five millimeters apart.

In accordance with the technique of the invention, the stone material remaining between the drilled holes is then carefully removed by scraping or other suitable methods. Care is taken not to scrape the stone material any deeper than the depth of drilled holes. The resultant bottom portion of the stone extremity model 50 is thus not anymore an exact replica of the surface configuration of the patient's amputated limb extremity 18, but rather is specially contoured to take into consideration the tissue softness or consistency of the extremity. This allows an individualized fit of the prosthetic member sleeve to the soft tissue areas of the patient's amputated limb extremity 18. A tight but yet comfortable fit of the sleeve and the marginal rim thereof to the extremity 18 is thus assured. Additional sculpting may also be conducted to further conform the sleeve to the extremity 18. The stone model 50 is again placed into the sandal and the outline 52 is marked, as the original outline has been scraped away. Additionally, a groove is scraped in the circumferential top margin 52.

Figure 10:
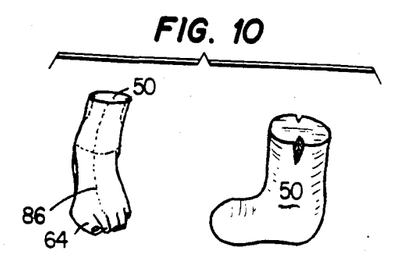
FIG. 10 illustrates the location of the equatorial division of wax model.

As shown in FIG. 10, a pair of fixation grooves 84 are scraped into that part of the stone extremity model extension 50. The purpose of the grooves 84 will be discussed below. The location of equator 86 on the composite temporary wax mold 64 and attached stone extremity model 50 is determined, which location divides the left and right parts of the composite model. The location of equator 86, however, is determined at those points which do not necessarily divide the left and right wax parts into equal halves, but rather is located at the place which provides the largest radial dimension outwardly from the wax model 64. As will be described below, the location of the equator 86 enables easy removal of the prosthetic member and the stone model 50 from the mold.

Continuing with the technique of the invention (FIGS. 11a and 11b), a sticky material 88 or other substance such as a clay is formed along the equator 86, on the entire top side thereof. The sticky substance 88 is formed with a sharp vertical surface 90 around the entire equatorial circumference of the wax model 64, as well as around that part of the attached stone extremity model 50 which protrudes from the wax model 64.

Figures 11A, 11B:
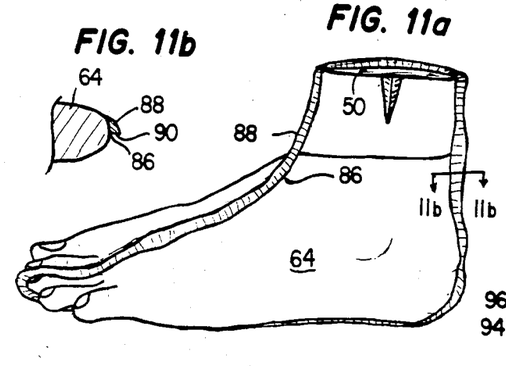
FIGS. 11a and 11b depict views of the wax model of the foot and the stone model with an equatorial barrier formed therearound.
Figure 12:
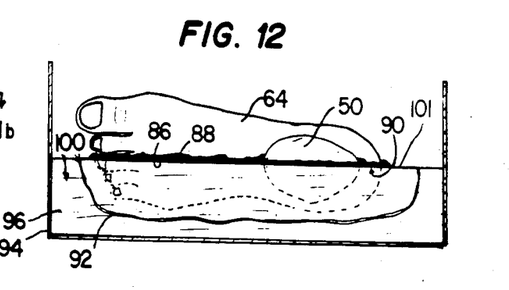
FIG. 12 shows the first half of the final mold.

A fiberglass screen sheet 92 is then pressed into a flask or box 94 filled with a slurry 96 of dental stone or plaster of paris. In practic,e the flask is a two part metal box with a lid. The fiberglass 92 provides reinforcement support when the slurry 96 hardens. The fiberglass sheet 92 assures that if the final stone mold 100 becomes cracked or broken during use, it will remain an integral structure. Of course, materials other than a fiberglass screen can be used. The composite wax model 64 and stone extremity model 50 are then pressed into the slurry 96. As noted from FIGS. 11 and 12, the temporary wax model 64 is turned sideways, such as would be if the patient were positioned on a side prone position. the composite unit is immersed into the slurry 96 up to the equator marks 96. It can be realized that the sticky substance 88 prvents the slurry 96 from contacting those areas above the equator marks 86. In this manner, when the slurry 96 hardens, an excellent definition of the mold half edge is formed, which edge can be abutted with a corresponding edge of the other mold half.

Figure 13:
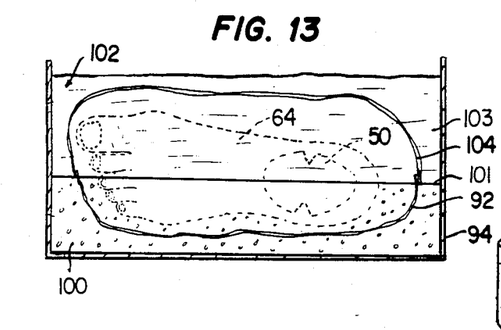
FIG. 13 shows the formation of the second half of the final mold.

Continuing with the technique for preparing the final mold, when the slurry 96 hardens the sticky substance 88 is removed, and a separator material such as Vaseline is applied to the face 101 of the first mold half 100. The purpose of the separator is to prevent the stone of the second mold half 102 from adhering to the first mold half 100 when poured thereon. This is shown in FIG. 13 of the drawings. The flask is filled with a stone slurry 103 to a depth substantially above the top surface of the wax model 64. While the stone slurry 103 of the second mold half 102 is still in a liquid state, a second fiberglass screen sheet 104 is pushed into the slurry 103.

Figure 14:
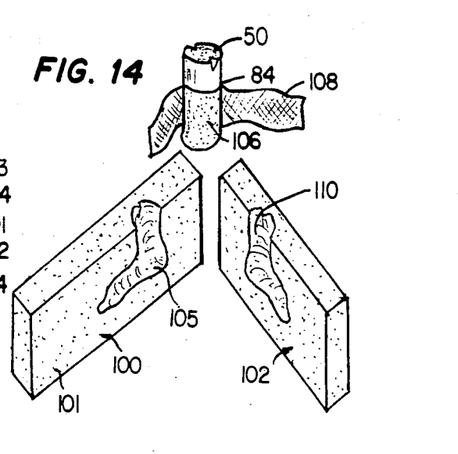
FIG. 14 illustrates the components of the final mold assembly prepatory to the silicone packing of the prosthetic foot member.

After the second mold half 102 has hardened, the mold halves are forced apart at the separator interface 101 as shown in FIG. 14. The stone extremity model 50 is separated from the wax model 64 in the same manner. The stone extremity model 50, as well as the mold halves 100 and 102 are then immersed into boiling water to remove the wax model 64. The preliminary wax model 64 is thereby destroyed. However, a highly accurate negative impression of the wax model 64 has been transferred to the interior surfaces 105 of the mold halves 100 and 103.

With this three-part mold construction 50, 100, 102, the prosthetic member is ready to be constructed using silicone material as the basis for the finished prosthetic member. The use of silicone is advantageous as it is easily formed into the shape desired, and it is durable and resistant to moisture. Also, silicone is well adapted for accepting colorations similar to flesh tones.

In forming the silicone prosthetic member, a layer of clear silicone 106 is first applied to the stone extremity model 50, up to the circumferential top margin 52. A layer of reinforcing material 108 such as perlon tricot is lightly pressed into the clear silicone 106. The reinforcement 108 provides the necessary strength and support of the shell of the prosthetic member for snugly receiving the amputated limb extremity 18. Other materials which are strong and resistant to stretching may be used with equal advantage.

Next, a mixture of the clear and white silicone material is prepared. Mixed within the mixture are colored pigments which match the lightest color of the patient's undamaged foot. In the preferred form of the invention, the color pigmentation constitutes Rayon flock particles. The entire mixture, which is of a gelatinous consistency, is packed into both opened mold halves 100 and 102 of the final stone mold. The stone extremity model 50 is positioned into the opening 110 previously formed in the mold halves 100 and 102. The mold halves 100 and 102 are then closed together, with the stone extremity model 50 interposed therebetween, and tightly clamped together under hydraulic pressure. Excess silicone material is squeezed out of the composite mold through the space between the stone extremity model 50 and the mold halves 100 and 102. The silicone mixture within the mold is allowed to cure for approximately sixteen hours. This time is sufficient to allow an exterior layer of the silicone to cure, while yet leaving the interior portion thereof uncured, and thus yet in a jelly state. The mold halves 100 and 102 are removed from the hydraulic pressure and opened, and the stone model 50 is removed, together with the silicon prothesis 112.

As noted above, the pressure exerted on the mold halves 100 and 102 forces the excess skin-colored silicone out of the mold halves 100 and 102, thereby forming a layer of skin-tone silicone adhering to the reinforcing layer 108. The silicone prosthetic member 112 can now undergo further processing. The mold halves 100 and 102, as well as the stone extremity model 50 are no longer needed, but are reusable in the event another silicone prosthetic member is desired. This is highly advantageous and represents an advance in this art as the entire foregoing procedure of constructing the mold need not be duplicated. As a result, additional protheses can be made for the same patient from this mold, at much reduced costs.

Figure 15:
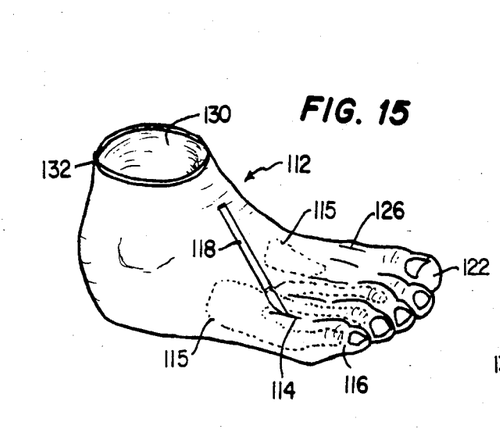
FIG. 15 illustrates the procedure for finishing the prosthetic member for proper flexing and bending capabilities.

The sixteen-hour curing time allows about 2-3 millimeters of the outer silicone layer to become cured. The majority of the silicone material interiorly located is yet uncured. Different compositions or types of prosthetic forming materials may necessitate different curing times to achieve the noted thickness of the outside cured layer. In order to provide a silicone prosthetic member material resiliency similar to that of the patient's flesh, a slit 114 is made in the silicone prosthetic member 112. FIG. 15 illustrates this step. The cut 114 may be made by a scalpel 118 through the cured silicone outer layer behind toe 116.

A desired amount of uncured silicone is then squeezed out of or extracted from the slit 114 to form hollow spaces 115 in desired areas. While the cut 114 is shown made from the top, it can also be made from the bottom of the prosthetic member 112. These hollow areas 115 allow the outside of the prosthesis and the third, fourth and fifth toe of the silicone prosthetic member 112 to be slightly compressed, as is necessary when wearing narrow shoes. This feature of the invention also allows the toes of the silicone prosthetic member 112 to react to flexing in a manner substantially the same as the toes of the uninjured foot. This is important, especially when the patient wears open-toed or narrow-sized shoes. After sufficient material is extracted from slit 114, the slit is closed and sealed with fresh silicone.

The silicone prosthetic member 112 is then immersed into hot water for further curing of the silicone material interior to the member 112. At two-hour intervals the silicone prosthetic member 112 is removed from the hot water and cooled. The flexibility behind the large toe 122 examined. A desired degree of resiliency behind the big toe 122 is advantageous for assisting the patient in walking. A springy resiliency behind the big toe 122, greater than that which exists behind the other toes, is desired to aid in propelling the patient while walking. In the event the degree of resiliency has not been achieved, the silicone prosthetic member 112 is again submerged in the hot water for a period of time to further cure the interior silicone. The degree of flexibility is again checked. If the desired degree of resiliency has been achieved, cut 126 is made by the scalpel 118 behind the big toe 122. The uncured silicone located below and behind the cut 126 is removed. The cut 126 is closed with silicone as above described, and remaining uncured silicone is cured in hot water.

In order to provide a natural flesh-like resiliency to the prosthetic member 112, the hollowed areas from which the gelatinous silicone was removed can be filled with a flexible, light material. Silicone foam can be injected or packed into the hollow areas 115 and allowed to cure. Other soft, lightweight filler materials can be used to achieve the same purpose.

The inside surface 130 of the prosthetic member shell 132 is ground with a dental grinding stone to remove any rough surfaces which may have inadvertently formed as a result of imperfections in the stone extremity model 50. A solution of clear silicone and xylene is prepared and poured into the prosthetic member shell 132. With this step, thin layer of silicone is deposited on the inner surface of the shell 132. The process of building up thin silicone layers is repeated until eventually the exposed reinforcement 108 is entirely covered on the inside surface 130.

It is important that any exposed areas of the reinforcement 108 be covered by silicone material, as any such unprotected areas will eventually become soiled or stained by the amputated limb extremity 18. The grinding described above on the inside surface 130 roughens the shell 132 and provides a mechanical connection of the cured silicone to the newly deposited silicone material.

Any undesired protrusions existing on the outside surface of the silicone prosthetic member 112 may also be removed with a grinding stone. A thin line of undesired silicone material may also exist along the equator line 86, formed by the interface discontinuity of the stone mold halves 100 and 102. The entire outside surface of the silicone prosthetic member 112 is then lightly ground to provide a slightly roughened clean surface. Two thin layers of the silicone-xylene solution are spread evenly over the entire outside surface of the prosthetic member 112. Areas which may have been excessively roughened by the grinding process are smoothened with a thicker solution of silicone and xylene.

Pigment colors or flocks are again dissolved in a silicone-xylene solution and applied with an air brush to the outer surface of the silicone prosthetic member 112. The color is selected to blend into the color of the ankle of the injured foot, and to match the color of the uninjured foot. Color variations in the prosthetic member 112, such as veins, the whites of the toenails, and other areas are painted on the prosthetic member 112 with a brush. On the general outside surface of the silicone prosthetic member 112, alternate layers of pigmented and clear silicone are applied to create a depth effect which creates a human-appearing skin. Moreover, when desired, hair or other synthetic fibers can be added within the layers to create a natural appearance. The colors are protected with several layers of clear silicone to form a coating for protecting the pigmented layers from scuffing or other abrasive wear.

Figure 16:
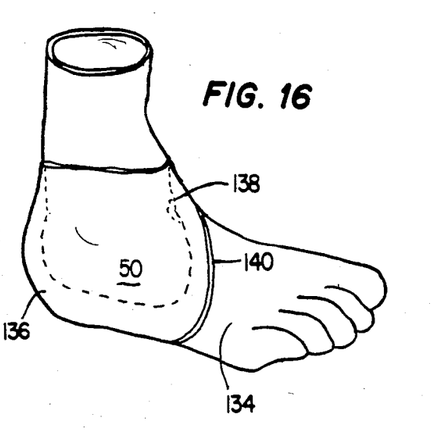
FIG. 16 illustrates the component parts of a non-personalized prosthetic foot member.

As an alternative to the foregoing, a less individualized prosthetic member can be formed by semiautomatic techniques. As shown in FIG. 16, the front portion of the foot 134 can be produced separately from the lower leg part 136. Once a mold has been constructed in accordance with the foregoing, a large number of prosthetic front feet parts 134 can be formed, even though there is not an exact resemblance between the corresponding extremities. The foot part 134 can thus be formed in the absence of the stone extremity model 50. An individualized fit of the lower foot part 134 to the amputated limb extremity 18 of the patient can be accomplished by forming the individual stone extremity model 50 for each patient in accordance with the foregoing. A lower leg shell 136 can then be formed separate from the lower foot part 134, and the parts mated together later where shown by reference character 140.

Conventionally available adhesives, and even fresh silicone can be used to fix the parts 134 and 136 together. In the embodiment shown in FIG. 16, the leg shell 136 and the foot part 134 are fixed together by forming a hollowed-out cavity 138 within the foot part. In accordance with this alternative technique, an individualized fitting prosthetic member can be formed and fitted to a mass produced non-personalized front foot 134. This is highly advantageous in those situations where the patient wears a shoe or foot covering, and the prosthetic member is rarely visible to others. The prosthetic member, being made of silicone or other suitable material, greatly facilitates the mobility of the patient, the physical appearance being a secondary concern. Indeed, the cost of a prosthetic member can be reduced by eliminating the sculpting, mold making the skin coloring and the other described time-consuming cosmetic measures.

It can be seen from the foregoing that an improved technique has been provided for forming prosthetic members, both of the individualized and the non-individualized types. It should be understood, however, that the foregoing is only exemplary of the techniques utilized in providing a finished prosthetic member. These techniques may be employed to form many other members of the human anatomy susceptible to artificial manufacture, e.g. hands, fingers, ears, etc. Also, very life-like models can be made for laboratory or educational purposes. Also, many of the techniques disclosed herein may be advantageously integrated into the prior art techniques, without employing all the techniques disclosed herein.

The foregoing technique can be simplified in certain instances where a second party donor is available having an uninjured body part similar in shape, size and appearance as the injured body part of the patient. In this case, a model of the donor's body part can be made using the techniques described above, without the need to mentally transform mirror images and sculpt a preliminary wax model.

With this alternative technique, tissue or paper is wrapped around the donor's pertinent body part to form a space, such as accomplished above with socks. Plaster bandages are wrapped around the spacer tissue and allowed to dry to form the rigid shell. A dental alginate or other contour conforming substance is placed around the inside of the shell and the donor's body part inserted therein. This forms a negative impression of the body part within the contour conforming substance. The body part is then carefully withdrawn and the substance is allowed to set. Molten wax is swirled around in the contour conforming negative impression until a desired thickness of wax is obtained. The contour conforming substance is then removed. Corrections may be made in the wax model to match the patient's features. With the alginate-wax fabrication steps, the impression is thereby transferred to the outside surface of the wax. Moreover, the wax model is of the same shape and size as the donor's part.

An impression of the patient's stump or injured member is then formed using the tissue paper, plaster bandages, alginate and slurry to form a stone model. In forming a foot prosthesis, for example, the same steps set forth above are repeated to form the stone model shown in FIG. 14. It can be appreciated that with a suitable donor, the fabrication of a prosthetic member can be expedited.

Therefore, in any prosthetic member formed according to the foregoing, many changes can be made which are not relevant to the novel features taught by the invention. Bearing this in mind, the specific techniques and embodiment disclosed herein are intended to be merely exemplary of the invention and not restrictive thereof since various modifications readily apparent with those familiar with the art can obviously made without departing from the spirit and scope of the invention as claimed hereinbelow.

What is claimed is:

1. A method for fabricating a prosthetic limb member for replacing a missing limb member by fabricating the prosthetic member substantially identical to an uninjured member, comprising the steps of:

forming a preliminary negative impression mold by forming an oversized rigid shell around the uninjured member and around the injured member sufficient to provide a spacing between the shells and the respective members;

filling the shells with a contour-conforming material;

inserting the uninjured member and the injured member into the respective preliminary negative impression molds in such a manner that the contour-conforming material fills a uniform space between the shells and the respective uninjured and injured members so that an uneven shrinkage of said contour-conforming material is avoided, and thereby resulting in an impression on the inside surfaces of the negative impression molds;

forming respective first models of the uninjured member and the injured member using the preliminary negative impression molds by pouring therein a material which solidifies and acquires on the outside surfaces thereof the impressions of the respective uninjured and injured members;

sculpting a second model of an image of the uninjured member having mirror image characteristics of the first model of the uninjured member;

forming a permanent negative impression mold having a cavity and an opening using the sculpted second model;

placing the first model of the injured member partially within the opening of the permanent negative impression mold of the uninjured member; and forming the prosthetic member by filling the permanent negative impression mold with a prosthetic forming material so that the material also surrounds the first model of injured member, whereby the prosthetic member has integral therewith a sleeve which has an inside surface thereof contoured according to the injured member.

2. The method of claim 1 wherein the sculpting step is carried out by sculpting the characteristics in a material having properties of wax.

3. The method of claim 1 further including forming the permanent negative impression mold with an internal cavity and forming said permanent negative impression mold in a plurality of parts so that the parts can be separated without destruction for removing the prosthetic member from said cavity.

4. The method of claim 1 further including the step of measuring the consistency of tissue to which the prosthetic member is to be attached, an adjusting the contour surfaces of the first model of the injured member accordingly.

5. The method of claim 4 wherein the prosthetic member is formed for attachment over an extremity, and further including measuring the consistency of the tissue by depth measurements at selected areas over substantially the entire area of the extremity.

6. The method of claim 5 wherein the depth measurements are transferred to the first model of the injured member as a grid of closely-spaced holes having corresponding depths.

7. The method of claim 1 further including forming a hollow area beneath the exterior surface of the prosthetic forming material in a selected area of the prosthetic member to provide flexibility.

8. The method of claim 7 further including forming the prosthetic member of a material which is selectively curvable in stages, and initially curing an outer layer of the prosthetic forming material, and removing uncured material from the selected area.

9. The method of claim 8 further including curing the material of the prosthetic member surrounding the hollow area.

10. The method of claim 1 wherein the preliminary negative impression mold is formed from a body part of a person other than the person having the injured member.

11. A method for fabricating a prosthetic upper or lower extremity attachable to an injured extremity, and having the characteristics of a corresponding uninjured extremity, comprising the steps of:

forming a record of an indication of the orientation of the corresponding uninjured extremity by placing a paper against the uninjured extremity and preparing an outline thereof;

transferring the indication of the orientation to positional information of the injured extremity by rotating the paper about an edge so as to be located adjacent the injured extremity to form a mirror image of the outline aligned with the injured extremity;

forming a rigid jacket around the respective corresponding uninjured and injured extremity, and spaced from the respective uninjured and injured extremity a predetermined distance therearound;

forming a negative impression mold of the outer surface contour of the corresponding uninjured and the injured extremity by interposing a contour-conforming material in the space between the jacket and the corresponding uninjured and the injured extremity;

forming a permanent model of the corresponding uninjured and the injured extremity by filling each said negative impression mold with a material which hardens and receives thereon a permanent impression of the contour characteristics of each said negative impression mold;

constructing a temporary model of the uninjured extrmity having mirror image characteristics of the permanent model;

fixing the temporary model to the permanent model of the body extremity in an aligned manner using the rotated record;

forming a sectioned final mold by encasing the temporary model of the corresponding uninjured extremity to form a cavity and by encasing a portion of the permanent model of the injured extremity with a material which hardens and which has impressed on the cavity surfaces thereof the impressions of the temporary model and the portion of the permanent model of the injured extremity encased;

removing the temporary model from the sectioned mold;

assembling the sectioned mold together with the permanent model of the injured extremity interposed at least partially therein; and packing a prosthetic forming material into the sectioned mold and at least partially around the permanent model of the injured member to thereby form the prosthetic member.

12. The method of claim 11 further including internally reinforcing the sections of the sectioned mold.

13. The method of claim 11 further including contouring the outer surfaces of the permanent model of the injured extremity according to the tissue consistency of the extremity.

14. The method of claim 13 further including sampling the tissue consistency of the patient's injured extremity at selected locations.

15. The method of claim 14 wherein the sampling includes applying an inward pressure to the injured tissue and measuring the amount of tissue depression.

16. The method of claim 15 further including applying a uniform inward pressure at the selected locations.

17. The method of claim 15 further including replicating tissue consistency of the injured extremity on the permanent model of the injured extremity at corresponding locations thereon.

18. The method of claim 17 wherein the replicating step includes drilling holes in the permanent model of the injured extremity at depths corresponding to the amount of tissue depression.

19. The method of claim 18 further including removing the permanent model of the injured extremity material laterally between the drilled holes, and to a depth defined by the bottom of the drilled hoels.

20. A method for fabricating a prosthetic body part to provide an improved fit to a body extremity, comprising the steps of:
   forming a sleeve conencted to the prosthetic body part, the sleeve being fittable over a portion of the extremity;
   determining the tissue consistency of the extremity of closely spaced selected areas thereon by applying an inward pressure at each such selecetd area and measuring the amount of associated tissue depression and recording each such measurement and the associated area; and
   forming on the inside of the prosthetic body part sleeve, at selected locations corresponding to the selected lcoations of the tissue measurements, areas which are contoured according to the measurements of the tissue depression.

21. The method of claim 20 further including initially forming a model of the extremity having an outer surface contoured according to the contour of the extremity.

22. The method of claim 21 further including adjusting the contoured surface of the model in accordance with the tissue consistency of the extremity.

23. The method of claim 22 further including drilling a plurality of holes in the extremity model to a depth corresponding with the depth of measurement of the tissue consistency, and removing the model material laterally between the drilled holes.

24. The method of claim 23 further including selecting areas for determining tissue consistency in a grid of locations spaced about five millimeters apart.

25. A method for fabricating a prosthetic member in the likeness of a body part, comprising the steps of:
   forming a prosthetic member in the likeness of a body part; and
   forming a hollowed area within the member at a preselected area which is subject to flexing.

26. The method of claim 25 further including forming the prosthetic member with a gelatinous material which is selectively hardenable;
   curing the outer surface of the gelatinous material;
   puncturing the cured layer of gelatinous material proximate the selected area; and
   extracting a desired amount of uncured gelatinous material to thereby form the hollow area.

27. The method of claim 26 further including removing uncured gelatinous material from other selected areas not susceptible to flexing to thereby reduce the weight of the member.

28. The method of claim 26 further including curing the remaining gelatinous material after forming the hollow areas.

29. The method of claim 25 further including filling the hollow areas with a flexible, light weight material.

30. The method of claim 26 further including forming the prosthetic member with a silicone material.

31. The method of claim 25 further including forming a prosthetic member in the likeness of a foot, and forming said hollow areas in an area behind selected toes.

32. The method of claim 25 further including forming a prosthetic member in the likeness of a hand, and forming said hollow areas in an area behind selected fingers.

33. A method for fabricating a prosthetic foot member for attachment to an ankle extremity, comprising the steps of:
   forming a pliable sleeve part of the prosthetic member having an inner surface for individual conformance to the contour characteristics of the ankle extremity so as to be individually and conformably attachable thereto;
   forming said sleeve part having an outer surface with size, shape and color characteristics which are characteristic of the ankle extremity so that said sleeve appears as a life-like extension of said ankle extremity;
   forming a prosthetic foot member having general characteristics of a foot;
   forming a hollowed area within the foot member at a preselected internal area which is subject to flexing; and
   attaching the sleeve part to the foot member so that a general appearing prosthetic foot member can be attached to the ankle extremity with an individualized fit, and so that said prosthetic foot member undergoes flexing during walking motions to facilitate mobility.

34. The method of claim 33 wherein the sleeve part is formed by forming a negative impression mold of the extremity with the inside surface thereof having the contour characteristics of the ankle extremity;
   forming a model of the ankle extremity by filling the negative impression mold with a material which hardens and which acquires on the outside surface thereof the characteristics of the negative impression mold;
   forming the prosthetic sleeve part around the model so that the inner surface of the sleeve conforms to the individual characteristics of the ankle extremity; and
   attaching the sleeve to the prosthetic foot member.

35. The method of claim 34 further including forming contoured surfaces in the sleeve which correspond to a tissue consistency of the ankle extremity.

36. The method of claim 35 wherein protrusions are formed in contoured surfaces of the sleeve in areas corresponding to areas of soft tissue consistency on the ankle extremity.

* * * * *